(12) United States Patent
Banick et al.

(10) Patent No.: US 7,125,424 B2
(45) Date of Patent: Oct. 24, 2006

(54) SKELETAL STABILIZATION IMPLANT

(75) Inventors: Christopher M. Banick, Orono, MN (US); Jack A. Dant, St. Paul, MN (US); David A. Hanson, St. Louis Park, MN (US); Rodney L. Houfburg, Prior Lake, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 0 days.

(21) Appl. No.: 10/261,082

(22) Filed: Sep. 27, 2002

(65) Prior Publication Data

US 2003/0093153 A1    May 15, 2003

Related U.S. Application Data

(60) Provisional application No. 60/325,804, filed on Sep. 28, 2001.

(51) Int. Cl.
*A61F 2/44* (2006.01)

(52) U.S. Cl. .................. 623/17.11; 623/17.16

(58) Field of Classification Search .. 623/17.11–17.19, 623/16.11, 23.51
See application file for complete search history.

(56) References Cited

U.S. PATENT DOCUMENTS

| | | | |
|---|---|---|---|
| 4,416,629 A * | 11/1983 | Mozsary et al. ............. | 433/174 |
| 4,904,261 A | 2/1990 | Dove et al. | |
| 5,015,817 A | 5/1991 | Kranz | |
| 5,250,048 A * | 10/1993 | Gundolf ..................... | 606/69 |
| 5,298,254 A | 3/1994 | Prewett et al. | |
| 5,716,415 A * | 2/1998 | Steffee ..................... | 623/17.16 |
| 5,728,159 A | 3/1998 | Stroever et al. | |
| 6,033,438 A | 3/2000 | Bianchi et al. | |
| 6,102,912 A * | 8/2000 | Cazin et al. ................. | 606/61 |
| 6,143,033 A | 11/2000 | Paul et al. | |
| 6,174,311 B1 | 1/2001 | Branch et al. | |
| 6,387,130 B1 * | 5/2002 | Stone et al. ............. | 623/17.16 |
| 6,468,311 B1 | 10/2002 | Boyd et al. | |
| 6,475,218 B1 * | 11/2002 | Gournay et al. ............. | 606/61 |
| 6,613,090 B1 * | 9/2003 | Fuss et al. ............... | 623/17.11 |
| 2001/0031254 A1 | 10/2001 | Bianchi et al. | |
| 2002/0026244 A1 * | 2/2002 | Trieu | |
| 2002/0106393 A1 | 8/2002 | Bianchi et al. | |
| 2003/0093153 A1 | 5/2003 | Banick et al. | |
| 2003/0149438 A1 * | 8/2003 | Nichols et al. | |

FOREIGN PATENT DOCUMENTS

| | | |
|---|---|---|
| DE | 200 17 962 U1 | 2/2001 |
| EP | 0 366 945 A1 | 5/1990 |
| WO | WO 94/05235 | 3/1994 |
| WO | WO 98/17209 | 4/1998 |
| WO | WO 99/09914 | 3/1999 |
| WO | WO 00/24327 | 5/2000 |
| WO | WO 00/40179 | 7/2000 |
| WO | WO 00/41654 | 7/2000 |
| WO | WO 00/62719 | 10/2000 |
| WO | WO 00/74608 A1 | 12/2000 |
| WO | WO 01/70137 A2 | 9/2001 |

* cited by examiner

*Primary Examiner*—Bruce Snow
*Assistant Examiner*—Cheryl Miller
(74) *Attorney, Agent, or Firm*—Wood, Herron & Evans, LLP (57) ABSTRACT

A spinal implant is described in this disclosure. The implant includes first and second pieces separated by a controlled break location. Spinal implant kits having multiple spinal implant pieces derived from a common source also are disclosed.

22 Claims, 10 Drawing Sheets

SKELETAL STABILIZATION IMPLANT

This application claims priority to U.S. Provisional application 60/325,804, filed Sep. 28, 2001.

FIELD OF THE INVENTION

The present invention relates generally to skeletal implants. More particularly, the present invention relates to implants for stabilizing intervertebral joints.

BACKGROUND OF THE INVENTION

Chronic back problems cause pain and disability for a large segment of the population. In many cases, chronic back problems are caused by intervertebral disc disease. When an intervertebral disc is diseased, the vertebrae between which the disc is positioned may be inadequately supported, resulting in persistent pain. Stabilization and/or arthrodesis of the intervertebral joint can reduce the pain and debilitating effects associated with disc disease.

Spinal stabilization systems and procedures have been developed to stabilize diseased intervertebral joints and, in some cases, to fuse the vertebrae that are adjacent the diseased joint space. Most fusion techniques include removing some or all of the disc material from the affected joint, and stabilizing the joint by inserting an implant (e.g., a bone graft or other material to facilitate fusion of the vertebrae) in the cleaned intervertebral space.

Spinal implants can be inserted into the intervertebral space through an anterior approach, a posterior approach, or postero-lateral approach. The anterior approach involves a surgeon seeking access to the spine through the front (i.e., abdominal area) of the patient. The posterior approach involves a surgeon seeking access to the spine through the back of the patient. The postero-lateral approach is similar to the posterior approach with access coming more from either or both sides of the patient. A variety of different anterior, posterior and postero-lateral techniques are known.

It is often an advantage to use the posterior approach because such an approach typically involves a smaller and less intrusive opening than those required by anterior approach techniques. Because a posterior approach involves a smaller opening, two or more implants are often used in this approach as compared to using a single larger implant. For example, in one technique, adjacent vertebral bodies are stabilized by implanting separate implants between the vertebral bodies on opposite sides of a sagittal plane passing through the midline of the vertebral bodies. When using multiple implants to support adjacent vertebrae, it is desirable for the implants to have similar or identical mechanical properties so that uniform support is provided on both sides of the sagittal plane. In some instances, it also is desirable for the implants to have similar or identical biologic properties (e.g., to reduce the risk of tissue rejection and to enhance the uniformity of creeping substitution).

SUMMARY OF THE INVENTION

One aspect of the present invention relates to skeletal implants and skeletal implant kits adapted to ensure that multiple implants used to support opposing vertebrae have been derived from the same source.

A variety of other aspects of the invention are set forth in part in the description that follows, and in part will be apparent from the description, or may be learned by practicing the invention. The aspects of the invention relate to individual features, as well as combinations of features. It is to be understood that both the foregoing general description and the following detailed description are exemplary and explanatory only and are not restrictive of the invention as claimed.

DETAILED DESCRIPTION

The present invention is directed to skeletal implants, skeletal implant kits and methods for placing implants between bones desired to be fused. It is preferred for the implants to be used for vertebral/spinal applications such as fusing cervical, thoracic and/or lumbar intervertebral joints. In the case of fusing an intervertebral joint, implants in accordance with the principles of the present invention can be implanted using an anterior, posterior or postero-lateral approach to the patient's vertebrae.

As used herein, an "implant" includes any implant suitable for facilitating fusion between adjacent bones and includes implants prepared from known implant materials including, non-bone material such as titanium, stainless steel, porous titanium, bio-glass, calcium phosphate, ceramic, carbon fiber-based polymers, biodegradable and polymers. However, it is preferred for implants in accordance with the principles of the present invention to be derived from natural bone tissue (e.g., allograft and xenograft bone). It is most preferred for implants in accordance with the principles of the present invention to be derived from natural bone such as from a cadaveric allograft bone source. For example, the implants can be derived by cross-sectioning cortical rings from cadaveric allograft bones such as femur, tibia or fibia bones. Alternatively, the implants can be formed/molded from ground, sintered or composite bone material. Bone tissue cut from a human femur bone is particularly suited for use in practicing the principles of the present invention. Xenograft bones (e.g., from a bovine source) also can be used.

The term "allograft" will be understood to mean a bone implant from a donor transplanted to a genetically dissimilar recipient of the same species. The term "xenograft" will be understood to mean a bone implant from a donor transplanted to a recipient of a different species.

Figure 1:
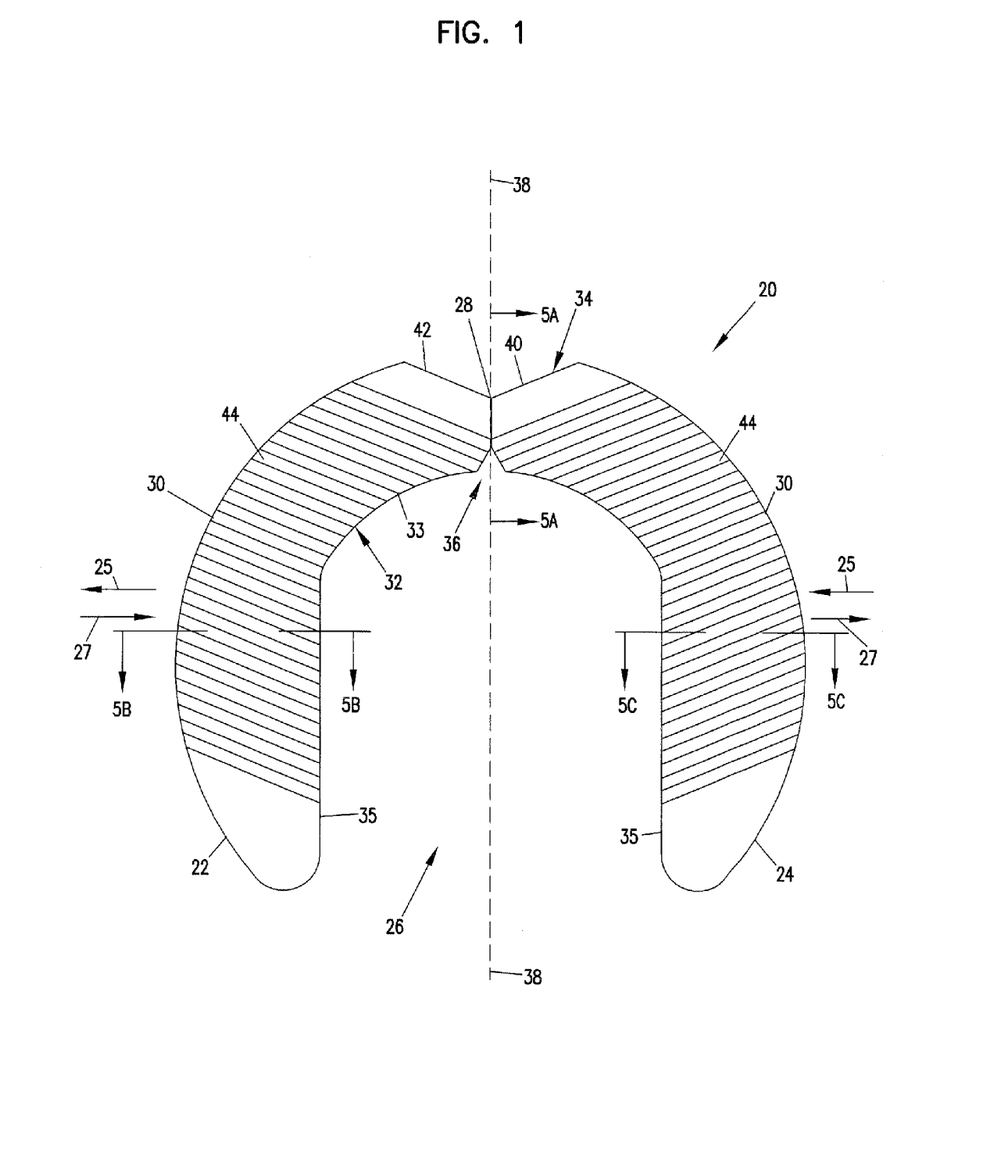
FIG. 1 is a top, plan view of one embodiment of a spinal implant in accordance with the principles of the present invention.
Figure 5A:
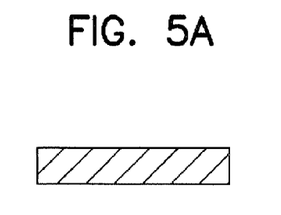
FIG. 5a is a cross-sectional view taken along section line 5a—5a of FIG. 1.
Figure 5B:
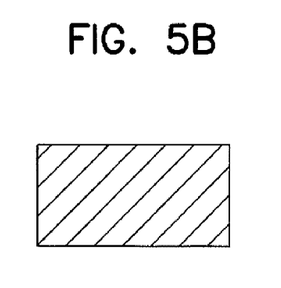
FIG. 5b is a cross-sectional view taken along section line 5b—5b of FIG. 1.
Figure 5C:
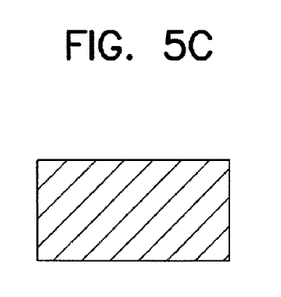
FIG. 5c is a cross-sectional view taken along section line 5c—5c of FIG. 1.

FIG. 1 shows a spinal implant 20 that is an embodiment of the present invention. As shown in FIG. 1, the spinal implant 20 includes first and second pieces 22, 24 (i.e., legs). The first and second pieces 22, 24 include portions opposing one another so as to define an inner pocket 26. The first and second pieces 22, 24 are integrally connected to one another at a central connection location 28. In one embodiment, the implant member 20 has a reduced cross-sectional area at the central connection location 28. The reduced cross-sectional area provides a controlled break location at the central connection location 28. As best shown in FIGS. 5a–5c, the region of reduced cross-sectional area at the central connection location 28 is smaller than nominal cross-sectional areas (average cross-sectional areas) of each of the first and second pieces 22, 24 of the spinal implant member 20.

Figure 2A:
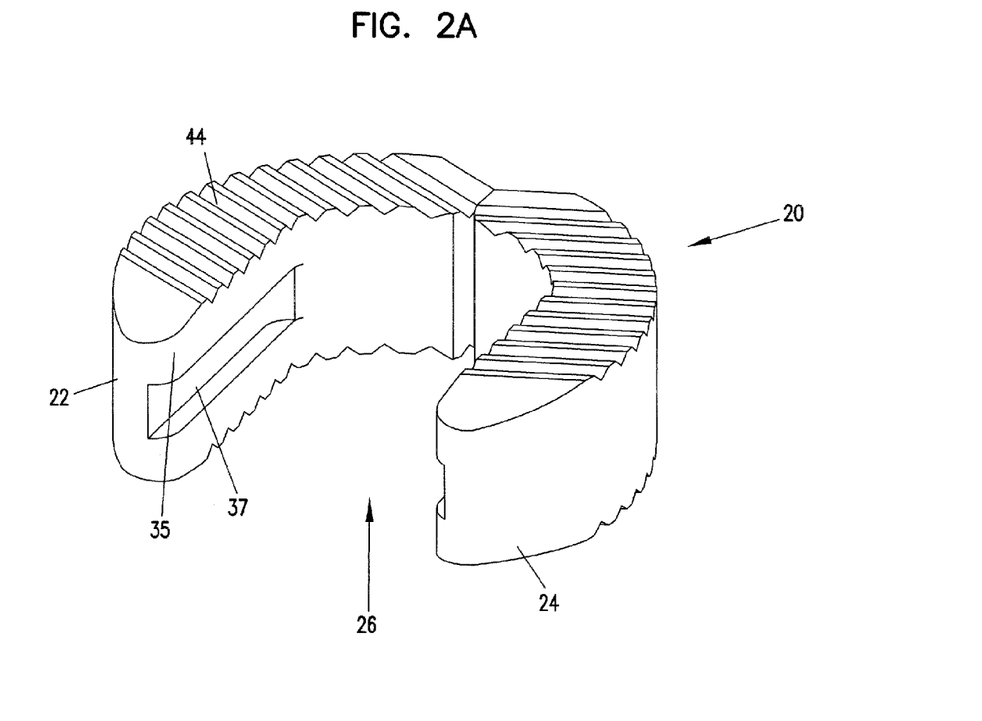
FIG. 2a is a front, top perspective view of the spinal implant of FIG. 1.
Figure 2B:
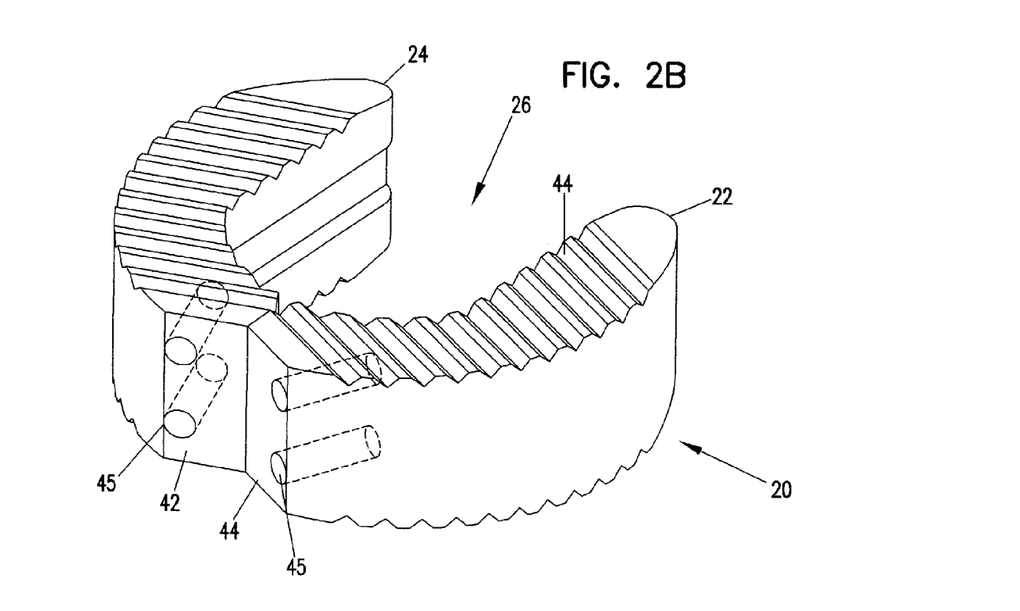
FIG. 2b is a rear, perspective view of the spinal implant of FIG. 1.
Figure 2C:
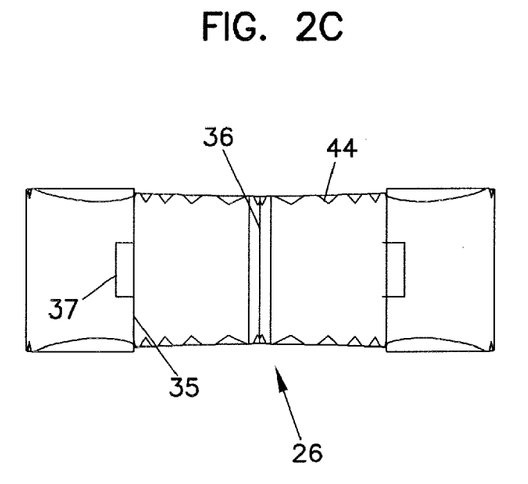
FIG. 2c is a front view of the spinal implant of FIG. 1.

As shown in FIG. 1, the spinal implant 20 has a generally "C" or "U" shape. The implant member 20 includes a convex outer boundary 30 and an inner boundary 32 having a concave portion 33 and opposing straight portions 35. As shown in FIGS. 2a and 2c, grooves 37 may be cut in the straight portions 35. A fixture fits within the grooves 37 to secure the implant during manufacture of the implant 20. The inner boundary 32 defines the pocket 26 of the implant 20.

Referring again to FIG. 1, a first notch 34 located at the outer boundary 30 of the implant 20 defines the reduced cross-sectional area at the controlled break location. A second notch 36 located at the inner boundary 32 of the spinal implant 20 also defines the reduced cross-sectional area. The first notch 34 is preferably larger than the second notch 36. Both notches 34 and 36 are aligned along an axis of symmetry 38 of the spinal implant 20.

Preferably, the controlled break location is configured to allow the first and second pieces 22, 24 of the implant member 20 to be manually broken or "snapped" apart without requiring the use of a tool. The controlled break structure ensures that the implant 20 will break at a predetermined location (e.g., at the axis of symmetry 38 for the embodiment of FIG. 1). The implant member 20 can be snapped by manually pulling the pieces 22, 24 apart by applying forces shown by arrows 25. Alternatively, the implant 20 can be snapped by manually pressing the pieces together as shown by arrows 27. Further, the implant member 20 can be broken by manually impacting the controlled break location against a relatively hard surface or edge such as the edge of a surgical instrument tray. In one embodiment, the reduced cross-sectional area provided at the controlled break location is at most 75 percent or, more preferably, about 50 percent of the nominal cross-sectional areas of each of the first and second pieces 22, 24. The controlled break locations can be defined by a variety of techniques for generating a "weaker" region at a desired location. Such weakened region can be formed by techniques such as notching, scoring, etching, cutting, mechanically perforating, laser perforating, etc. Alternatively, the controlled break location can be "weakened" by altering the mechanical properties of the implant material at the controlled break location by techniques such as radiation, demineralization or other techniques.

Figure 3:
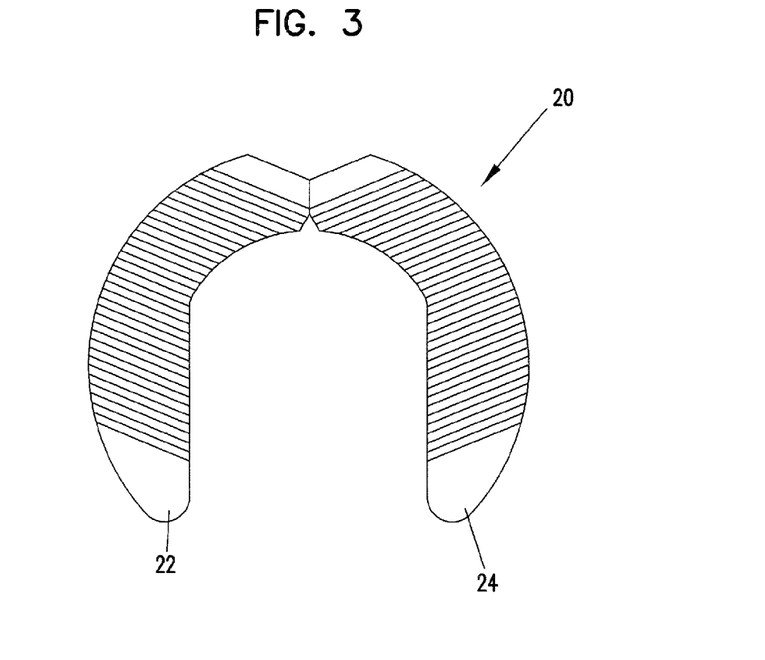
FIG. 3 shows the spinal implant of FIG. 1 split into two pieces.

FIG. 3 shows the spinal implant 20 after the implant has been manually "snapped" at the controlled break location. While it is preferred for the spinal implant 20 to be manually broken, it will be appreciated that tools such as forceps, knives, scissors, saws, clamps or other devices could also be used to split the implant 20 into multiple separate pieces. Further, impact tools such as hammers, chisels or the like also could be used. If tools are desired to be used, a controlled break location may, but need not, be provided. Instead, a line or other demarcation can be used to define a predetermined break location that provides a guide for using the tool.

Although the embodiment of FIG. 1 shows the controlled break location located at the central axis of symmetry of the implant 20, it will be appreciated that other embodiments can include controlled break locations offset from the center of the implant. Further, multiple controlled break locations can be provided to allow the implant to be broken into more than two pieces. Further, in another embodiment, an entire cortical ring is provided having two oppositely positioned break locations for allowing the implant to be snapped in half to form two separate implants.

Figure 4:
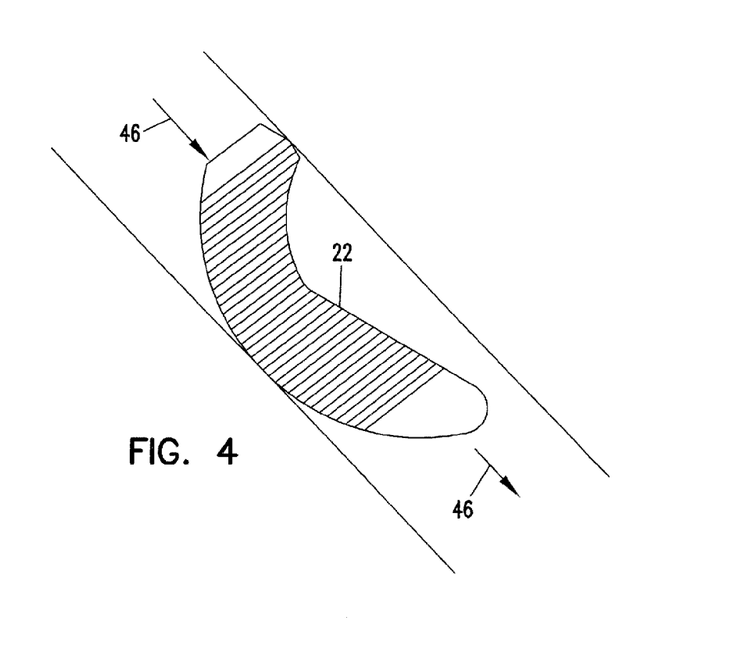
FIG. 4 shows one piece of the spinal implant of FIG. 1.
Figure 6A:
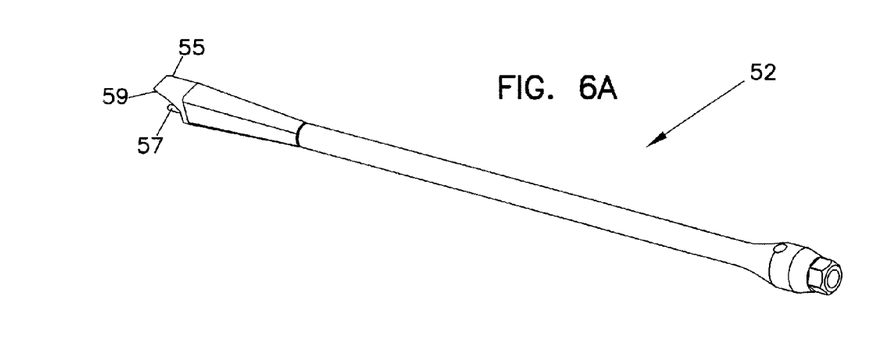
FIGS. 6a–6e show various views of an insertion tool suitable for inserting the spinal implant of FIG. 1.
Figure 6B:
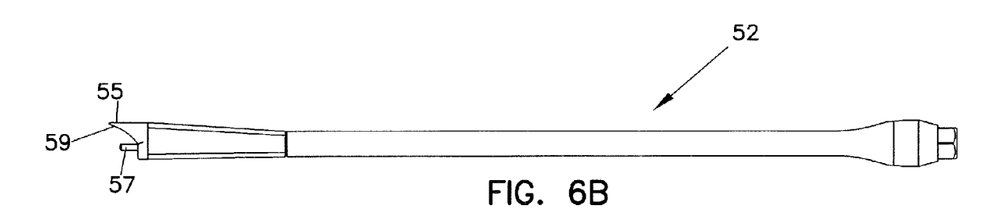
Figure 6C:
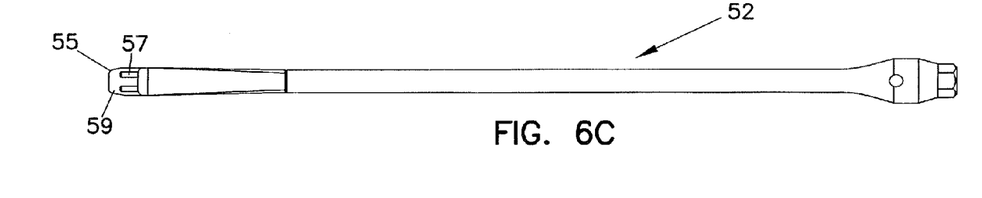
Figure 6D:
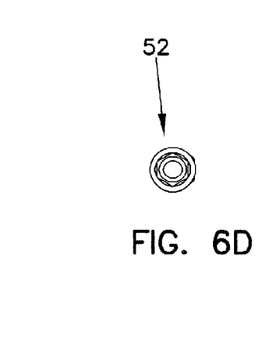
Figure 6E:
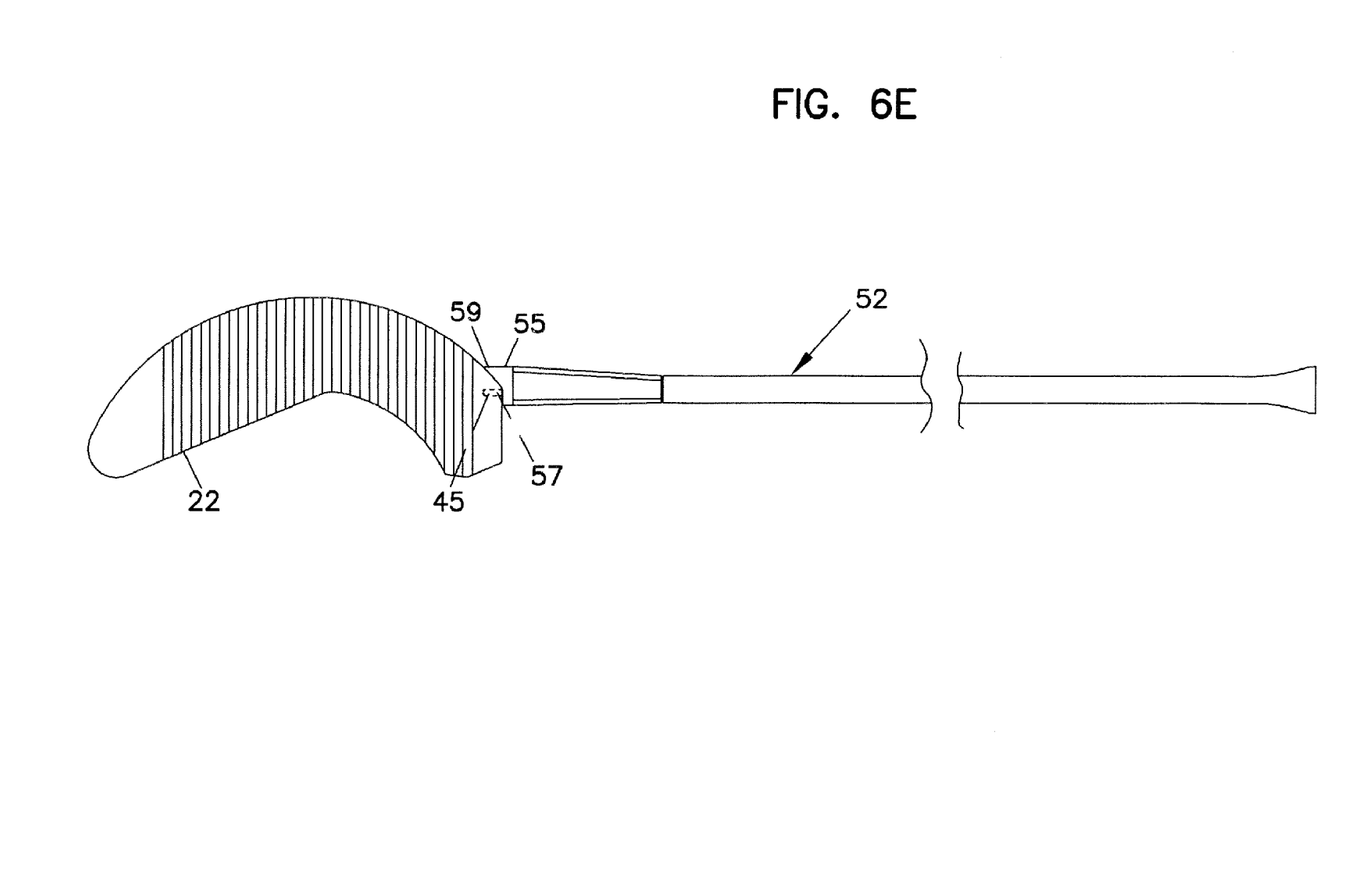

Referring again to FIG. 1, the first notch 34 is defined by first and second insertion force application surfaces 40, 42 aligned at an oblique angle relative to one another. The insertion force application surfaces 40, 42 are preferably aligned parallel to grooves 44 formed in top and bottom surfaces of the spinal implant 20. During implantation of the first and second pieces 22, 24, pins of an insertion tool (e.g., see insertion tool 52 of FIGS. 6a–6e) are placed in openings 45 (shown in FIGS. 2b and 6e) defined in the insertion force application surfaces 40, 42. During insertion, insertion forces are applied to the surfaces 40, 42 via the tool 52 to individually push the pieces 22, 24 into the intervertebral space. Particularly for posterior approach techniques, it is desirable for the pieces 22, 24 to be inserted in a direction requiring the smallest possible opening to be defined through the patient's posterior region. For example, arrow 46 of FIG. 4 shows a preferred direction of insertion. It is preferred for the insertion force surfaces 40, 42 to be perpendicularly aligned relative to the preferred insertion directions of their corresponding pieces 22, 24.

The grooves 44 of the implant 20 function to resist migration of the implant upon implantation between opposing bone surfaces. Other structures such as teeth, serrations, cross-cut serrations, notches, bumps, ridges, projections or other surface treatments could also be used.

Figure 2D:
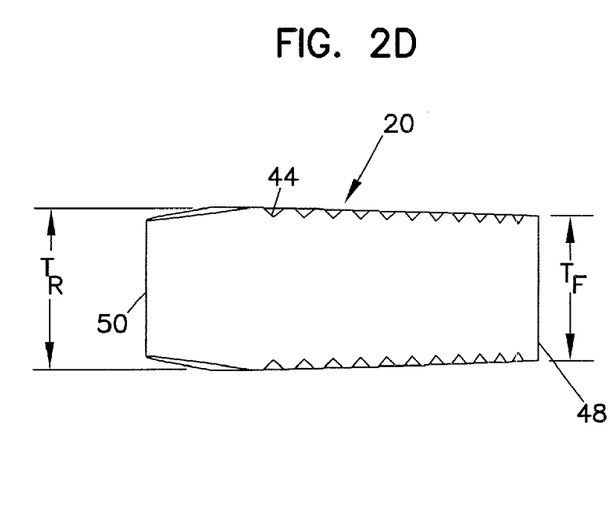
FIG. 2d is a side view of the spinal implant of FIG. 1.

While the implant 20 can have a constant thickness, it is preferred for the implant 20 to be slightly tapered. In one embodiment, the spinal implant 20 can be tapered about 3 degrees such that a front end 48 of the implant 20 has a thickness $T_f$ that is greater than a thickness $T_r$ located at a rear end 50 of the implant 20. The thicknesses $T_f$ and $T_r$ are labeled in FIG. 2d. In another embodiment, the front end 48 of the implant 20 may be chamfered to facilitate insertion.

FIGS. 6a–6e show an insertion tool 52 suitable for individually implanting the first and second pieces 22, 24 of the spinal implant 20 into the intervertebral space of a patient. The insertion tool 52 includes an insertion end 55 having two parallel pins 57 adapted to fit within the openings 45 defined by the force application surfaces 40, 42 of the implant pieces 22, 24. The tool 52 also includes a curved retaining surface 59 adapted to contact and complement a portion of the outer boundary 30 of the implant piece 22, 24 when the implant piece 22, 24 is mounted at the insertion end 55.

While other materials could be used, the spinal implant 20 is preferably derived from an allograft bone. In one embodiment, the implant 20 is a transverse cross-section from the femur of a cadaver, and includes a cortical ring. After the ring has been cross-sectioned, relatively soft bone tissue and marrow from the interior of the ring is preferably removed.

Next, a portion of the outer cortical ring is removed (e.g., by a technique such as mechanically cutting with a blade or abrasion tool, laser cutting, etching, etc.) to provide the open end of the pocket 26 of the "C" shaped implant 20 (see FIG. 1). Bone removal techniques are then also used to shape the outer and inner boundaries 30, 32 and to form the notches 34, 36. While the particular shape depicted in FIG. 1 is preferred, it will be appreciated that other shapes also could be used without departing from the principles of the present invention.

Figure 7:
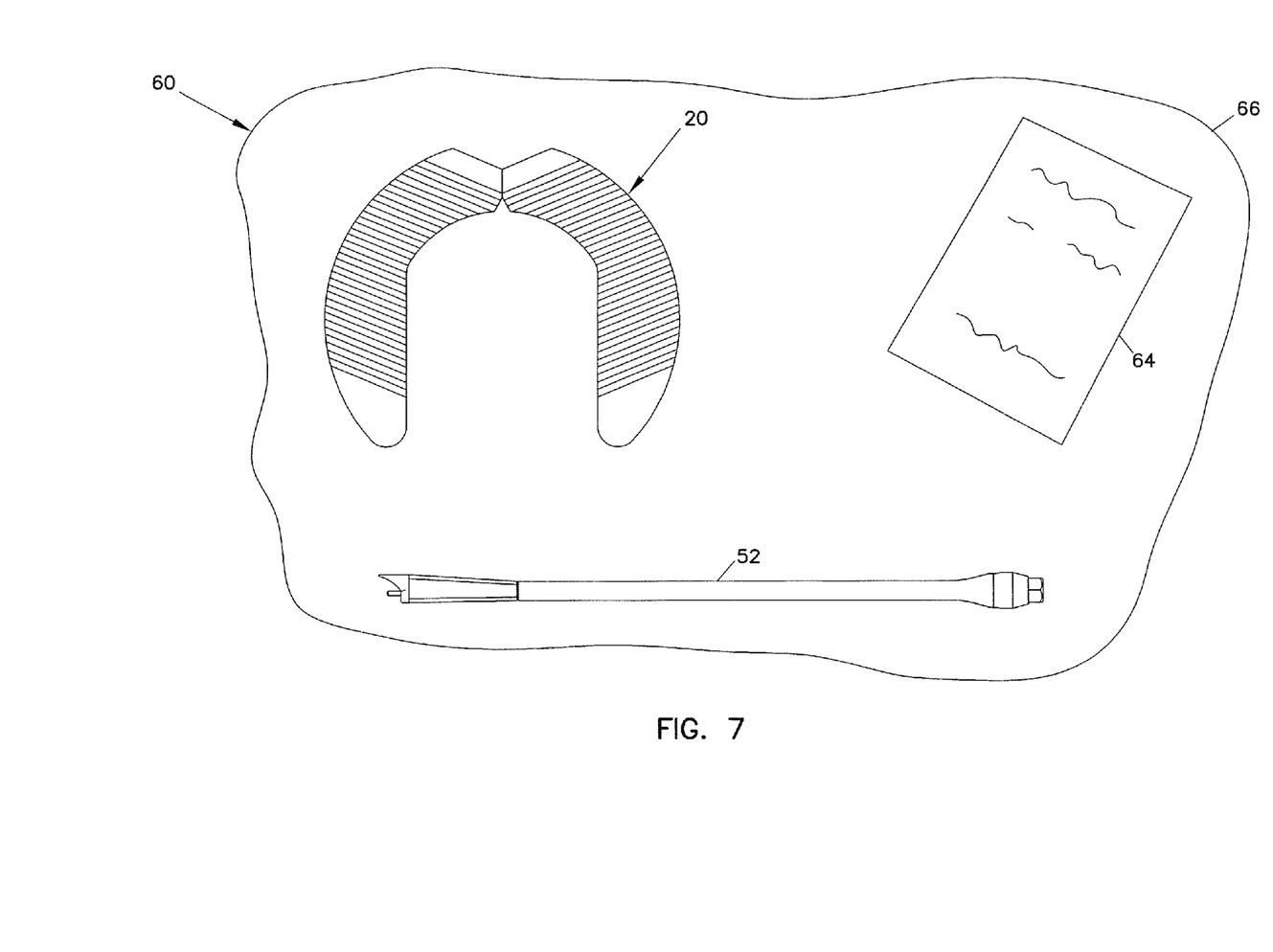
FIG. 7 is a kit incorporating the spinal implant of FIG. 1.

FIG. 7 illustrates a kit 60 that is an embodiment of the present invention. The kit includes the spinal implant 20, the insertion tool 52 and instructions 64 of use. The components are contained within a sterile package 66 (e.g., a bag, plastic container or other sealed holding configuration). In other embodiments, the kit includes the spinal implant 20, alone, within the sterile package.

Figure 8:
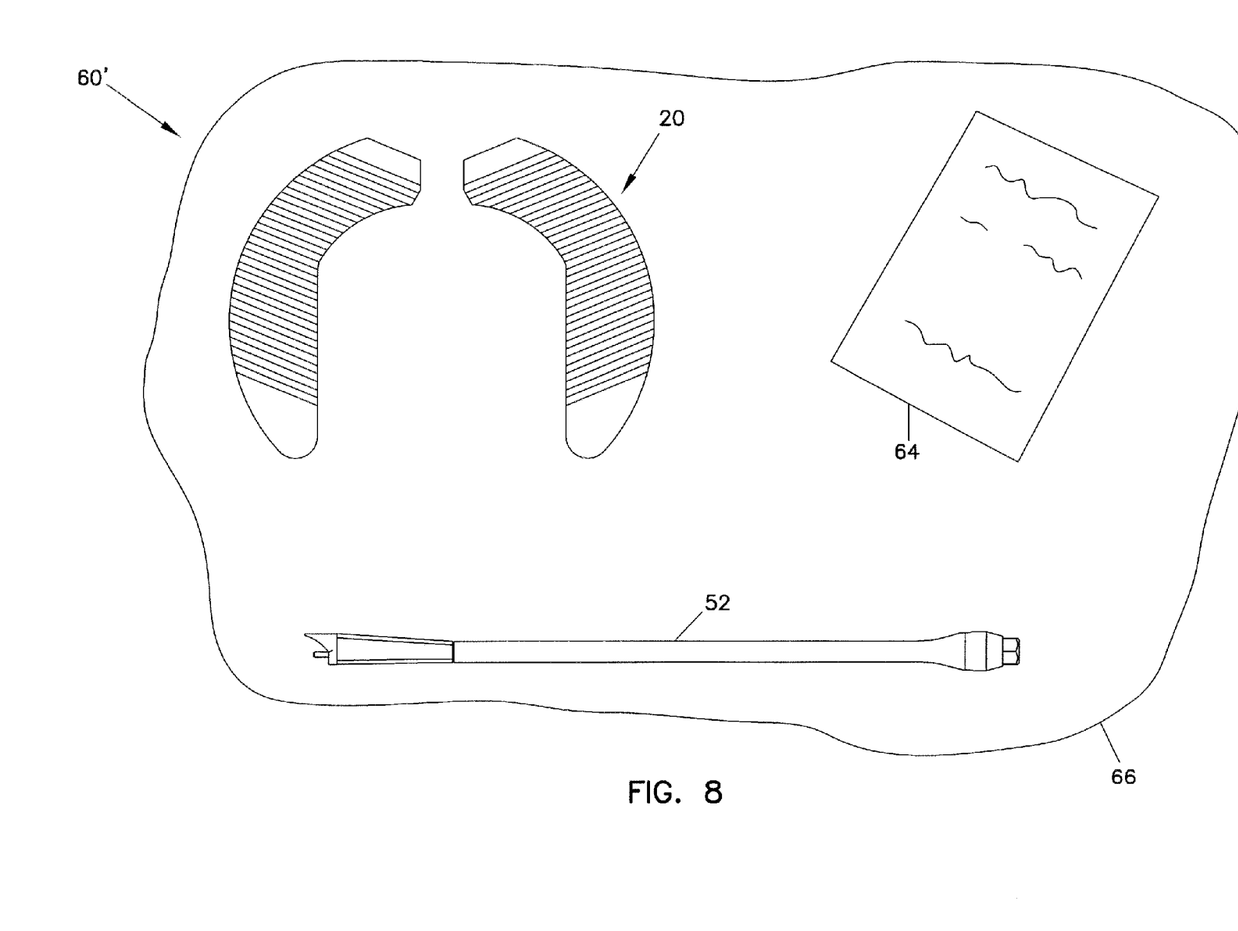
FIG. 8 is a kit incorporating the spinal implant of FIG. 1 with the spinal implant being separated into two pieces.

FIG. 8 shows another kit 60 that is an embodiment of the present invention. Similar to the embodiment of FIG. 7, the kit 60 includes the spinal implant 20, the insertion tool 52 and the instructions of use 64. Also similar to the embodiment of FIG. 7, the various parts are held within a sterile package 66. However, in the embodiment of FIG. 8, the spinal implant 20 has been pre-broken into the first and second pieces 22, 24. Preferably, both the first and second pieces 22, 24 were derived from the same source. For example, preferably the first and second pieces 22, 24 were provided from human bone tissue from the same cadaver. More preferably, the pieces 22, 24 were provided from the same cortical ring of the same bone. By packaging two or more implant pieces from the same source in one package, the surgeon that ultimately uses the implants will be assured that the pieces will exhibit similar or identical mechanical and biological properties. Further, by using bone pieces from the same donor, the risk of transferring disease to the patient is reduced by 50 percent as compared to using bone samples from two different donors. In other embodiments, the kit 60' includes the first and second pieces 22, 24, alone, within the sterile package.

The configuration of the implant of FIG. 1 provides similar advantages. For example, because the first and second implant pieces 22, 24 can be provided to a surgeon in an integrally connected configuration, the surgeon can be assured that the two pieces were derived from the same bone source. Further, the configuration of the controlled break location allows the surgeon to quickly and easily separate the two pieces without requiring a tool. In the event the implant is made of a non-bone material, the configuration ensures the surgeon that the implant pieces 22, 24 were manufactured in the same lot.

Figure 9A:
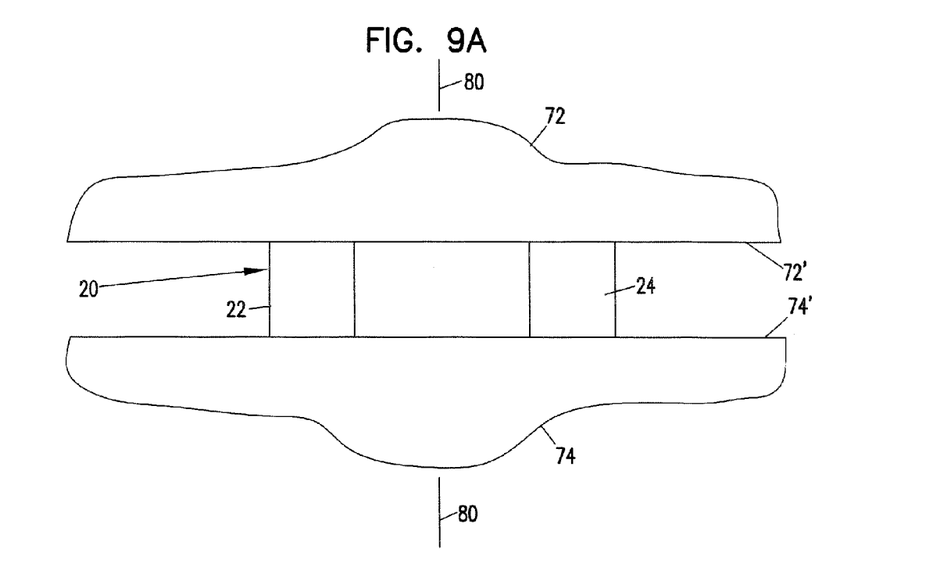
FIGS. 9a and 9b show the spinal implant of FIG. 1 inserted into the intervertebral space between two vertebrae.
Figure 9B:
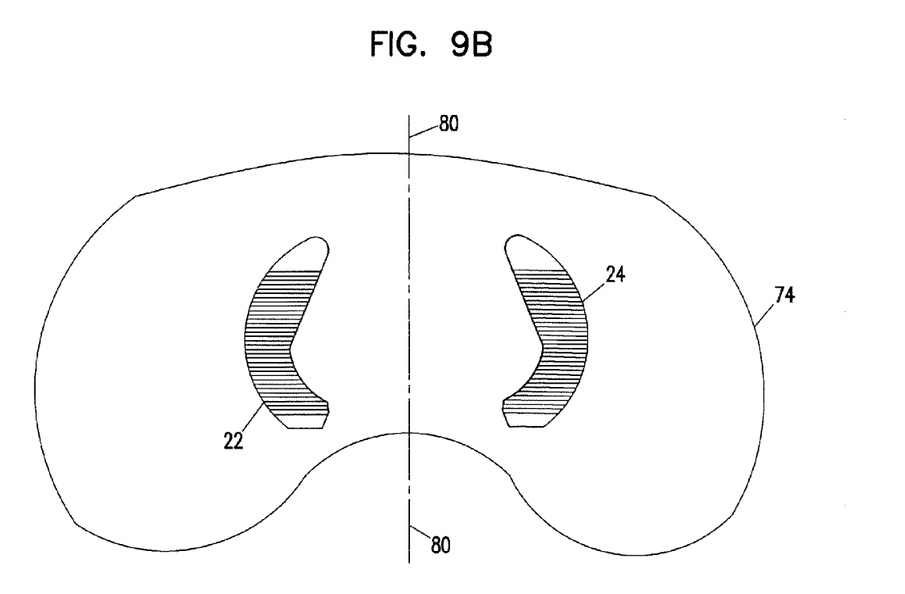

To implant the spinal implant 20, a diseased disc between two adjacent vertebrae 72, 74 is preferably removed using a conventional discectomy procedure (i.e., partial or complete discectomy). Opposing end plates 72' and 74' of the vertebrae 72, 74 are then preferably prepared to provide relatively flat contact surfaces. The end plates 72', 74' are then conditioned (e.g., with a rasp) to provide a more uniform and osteoconductive/osteoinductive site for the implant 20. After the implant site has been prepared, the sterile package of the kit 60 is opened, allowing the surgeon to access the implant 20. Preferably, the implant 20 is then manually "snapped" or broken into two pieces. One of the pieces 22 is then placed on the insertion tool 52. With the insertion tool, the surgeon inserts the first piece 22 into the cleared intervertebral space between the vertebrae 72, 74. Preferably, the first piece 22 is inserted using a posterior approach. As the first piece 22 is inserted, an insertion force is transferred through the insertion tool 52 to the insertion force surface 40 of the first implant piece 22. As shown in FIGS. 9a and 9b, the first implant piece 22 is preferably positioned on one side of a sagittal plane 80 that passes through the midline of the vertebrae 72, 74. Once the first implant piece 22 has been inserted, the tool 52 is withdrawn from the implant piece 22 and the second implant piece 24 is preferably inserted using the same procedure. However, the second implant piece 24 is preferably positioned on the opposite side of the sagittal plane 80. As mounted in the intervertebral space, the front end 48 of the implant 20 is preferably located at an anterior position relative to the rear end 50. To further promote fusion, additional bone material (e.g., cancellous allograft or autograft material) or other osteoconductive/osteoinductive material can be placed in the intervertebral space corresponding to the inner pocket 26 of the implant 20. This material can be placed in the intevertebral space before insertion of the first implant piece 22, after insertion of the first implant piece 22, but before insertion of the second piece 24, and/or after both implant pieces 22, 24 have been implanted.

It will be appreciated that the kit 60' can be used in essentially the same manner as the kit 60, except the kit 60' does not require the surgeon to manually break the spinal implant 20 into the separate first and second pieces 22, 24. In both embodiments, the surgeon can be assured that both the first and second pieces 22, 24 of the spinal implant 20 were derived from the same donor source.

With regard to the foregoing description, it is to be understood that changes may be made in detail without departing from the scope of the present invention. It is intended that the specification and depicted aspects of the invention may be considered exemplary, only, with a true scope and spirit of the invention being indicated by the broad meaning of the following claims.

We claim:

1. A skeletal implant comprising:
   first and second implant members, each comprising:
      a top surface adapted to engage and support an upper vertebra, and
      a bottom surface adapted to engage and support a lower vertebra; and
   a portion joining, and integral with, the first and second implant members, the portion having a convex outer boundary and a concave inner boundary and defining a first v-shaped notch at the outer boundary and a second v-shaped notch at the inner boundary, the first and second v-shaped notches configured to cause the joining portion to fracture at the tip of the first and second v-shaped notches under a torque applied to the implant members about an axis passing through the tip of the first and second v-shaped notches.

2. The implant of claim 1, wherein each implant member includes bone tissue.

3. The implant of claim 2, wherein the implant members are from an allograft bone source.

4. The implant of claim 1, wherein the first and second notches are configured to allow the joining portion to be manually broken and breaking the first and second implant members into separate pieces without the use of a tool.

5. The implant of claim 1, wherein the joining portion has a reduced cross-sectional area between the tips of the first and second notches as compared to nominal cross-sectional areas of the first and second implant members.

6. The implant of claim 5, wherein the reduced cross-sectional area is at most about 75 percent of the nominal cross-sectional areas of each of the first and second implant members.

7. The implant of claim 5, wherein the first and second implant members each include an insertion force application surface, the insertion force application surface of the first implant member being aligned generally perpendicular to an intended line of insertion of the first implant member, and the insertion force application surface of the second implant member being aligned generally perpendicular to an intended line of insertion of the second implant member.

8. The implant of claim 7, wherein the insertion force application surfaces of the first and second implant members define the first notch of the implant.

9. The implant of claim 1, wherein the first and second implant portions are symmetrically disposed with respect an axis of symmetry passing through the joining portion, and wherein the first and second notches are configured to cause the joining portion to fracture at the tips of the notches under forces applied to the implant members in directions transverse to the axis of symmetry.

10. A spinal implant comprising:
a spinal implant member including a first piece and an opposite second piece, each of which having a top surface for engaging and supporting an upper vertebra and a bottom surface for engaging and supporting a lower vertebra, the spinal implant member having a controlled break location positioned between the first and second pieces, the controlled break location having a convex outer boundary and a concave inner boundary, the break location including a first v-shaped notch at the outer boundary and a second v-shaped notch at the inner boundary, the controlled break location further including a region of reduced cross-sectional area between the first and second notches, the region of reduced cross-sectional area being smaller than nominal cross-sectional areas of each of the first and second pieces of the spinal implant member.

11. The spinal implant of claim 10, wherein the spinal implant member includes bone tissue.

12. The spinal implant of claim 11, wherein the spinal implant member is from an allograft bone source.

13. The spinal implant of claim 11, wherein the spinal implant member includes tissue from a femur bone.

14. The spinal implant of claim 10, wherein the reduced cross-sectional area is at most about 75 percent of the nominal cross-sectional areas of each of the first and second pieces.

15. The spinal implant of claim 10, wherein the first and second pieces each include an insertion force application surface, the insertion force application surface of the first piece being aligned generally perpendicular to an intended line of insertion of the first piece, and the insertion force application surface of the second piece being aligned generally perpendicular to an intended line of insertion of the second piece.

16. The spinal implant of claim 15, wherein the insertion force application surfaces of the first and second pieces are configured to define the first notch of the implant.

17. The spinal implant of claim 10, wherein the first notch is larger than the second notch.

18. The spinal implant of claim 17, wherein the controlled break location is provided at an axis of symmetry of the spinal implant member.

19. The spinal implant of claim 10, wherein the controlled break location is provided at an axis of symmetry of the spinal implant member.

20. The spinal implant of claim 10, wherein the spinal implant member is generally "C" shaped.

21. A spinal implant comprising:
a spinal implant member including a first piece and an opposite second piece, each of which having a top surface for engaging and supporting an upper vertebra and a bottom surface for engaging and supporting a lower vertebra, the spinal implant member having a controlled break location positioned between the first and second pieces, the controlled break location having a convex outer boundary and a concave inner boundary, the controlled break location including a first v-shaped notch at the outer boundary and a second v-shaped notch at the inner boundary, the controlled break location further including a region of reduced cross-sectional area between the first and second notches, the region of reduced cross-sectional area being smaller than nominal cross-sectional areas of each of the first and second pieces of the spinal implant member, wherein the first notch is larger than the second notch, wherein the first and second pieces are symmetrically disposed with respect an axis of symmetry passing through the controlled break location.

22. A spinal implant comprising:
a spinal implant member including a first piece and an opposite second piece, each of which having a top surface for engaging and supporting an upper vertebra and a bottom surface for engaging and supporting a lower vertebra, the spinal implant member having a controlled break location positioned between the first and second pieces, the controlled break location having a convex outer boundary and a concave inner boundary, the controlled break location including a first v-shaped notch at the outer boundary and a second v-shaped notch at the inner boundary, the controlled break location further including a region of reduced cross-sectional area between the first and second notches, the region of reduced cross-sectional area being smaller than nominal cross-sectional areas of each of the first and second pieces of the spinal implant member, wherein the first notch is larger than the second notch, wherein the spinal implant is generally C-shaped.

* * * * *

UNITED STATES PATENT AND TRADEMARK OFFICE
CERTIFICATE OF CORRECTION

PATENT NO. : 7,125,424 B2  Page 1 of 1
APPLICATION NO. : 10/261082
DATED : October 24, 2006
INVENTOR(S) : Christopher M. Banick et al.

It is certified that error appears in the above-identified patent and that said Letters Patent is hereby corrected as shown below:

IN THE CLAIMS:

In claim 9, column 7, line 17, change "with respect an" to --with respect to an--.

In claim 21, column 8, line 33, change "disposed with respect an" to --disposed with respect to an--.

Signed and Sealed this

Thirteenth Day of March, 2007

JON W. DUDAS
*Director of the United States Patent and Trademark Office*